United States Patent [19]

Antwiler

[11] Patent Number: 5,665,061

[45] Date of Patent: Sep. 9, 1997

[54] BIOLOGICAL/PHARMACEUTICAL METHOD AND APPARATUS FOR COLLECTING AND MIXING FLUIDS

[75] Inventor: Glen Delbert Antwiler, Lakewood, Colo.

[73] Assignee: Cobe Laboratories, Inc., Lakewood, Colo.

[21] Appl. No.: 364,471

[22] Filed: Dec. 27, 1994

Related U.S. Application Data

[63] Continuation-in-part of Ser. No. 928,040, Aug. 11, 1992, Pat. No. 5,378,277.

[51] Int. Cl.⁶ .................................................. A61M 5/00
[52] U.S. Cl. ............................... 604/4; 604/19; 604/65; 604/28
[58] Field of Search .......................... 604/4–6, 65–67, 604/19, 248, 30, 35, 118, 902; 210/645, 646

[56] References Cited

U.S. PATENT DOCUMENTS

| | | |
|---|---|---|
| 3,851,181 | 11/1974 | Heule . |
| 3,924,700 | 12/1975 | Lindsey et al. . |
| 3,955,573 | 5/1976 | Hansen et al. . |
| 3,964,484 | 6/1976 | Reynolds et al. . |
| 3,965,896 | 6/1976 | Swank . |
| 4,000,972 | 1/1977 | Braun et al. . |
| 4,002,170 | 1/1977 | Hansen et al. . |
| 4,193,004 | 3/1980 | Lobdell et al. . |
| 4,202,387 | 5/1980 | Upton . |
| 4,231,366 | 11/1980 | Schael . |
| 4,253,456 | 3/1981 | Schindler et al. . |
| 4,258,723 | 3/1981 | McCue et al. . |
| 4,267,837 | 5/1981 | Purdy et al. . |
| 4,275,726 | 6/1981 | Schael . |
| 4,370,983 | 2/1983 | Lichtenstein . |
| 4,385,630 | 5/1983 | Gilcher et al. . |
| 4,425,114 | 1/1984 | Schoendorfer et al. . |
| 4,481,827 | 11/1984 | Bilstad et al. . |
| 4,490,134 | 12/1984 | Troulner ............... 604/4 |
| 4,540,406 | 9/1985 | Miles . |
| 4,551,131 | 11/1985 | Miles et al. . |
| 4,592,743 | 6/1986 | Hjertman et al. . |
| 4,598,733 | 7/1986 | Kanno et al. . |
| 4,623,328 | 11/1986 | Hartranft . |

(List continued on next page.)

FOREIGN PATENT DOCUMENTS

| | | |
|---|---|---|
| 0 208 061A1 | 1/1987 | European Pat. Off. . |
| 0 438 703A1 | 7/1991 | European Pat. Off. . |
| 3 739 240 A1 | 5/1988 | Germany . |
| 2 009 862 | 6/1979 | United Kingdom . |
| 2 139 094 | 11/1984 | United Kingdom . |
| WO 88/06466 | 9/1988 | WIPO . |

OTHER PUBLICATIONS

"A Simple Autotransfusion System for Use in Abdominal Aortic Surgery," by A. Addison Barman et al., Surgical Rounds, Dec., 1987.

"Evaluation of a New Blood Autotransfusion Device," by John M. Toomasian et al., The Journal of Thoracic and cardiovascular Surgery, vol. 92, No. 5, pp. 936–942, Nov., 1986.

Operating instructions for "Thoratec Bloodstat Autotransfusion System," Thoratec Laboratories Corporation, 1983.

510 (k) Notification for "Thoratec Intraoperative Autotransfusion System," Thoratec Laboratories Corporation, Supplemental Submission, Jul. 25, 1983.

*Primary Examiner*—Mark O. Polutta
*Attorney, Agent, or Firm*—Finnegan, Henderson, Farabow, Garrett & Dunner, L.L.P.

[57] ABSTRACT

A blood circulation apparatus includes a suction wand for receiving blood from a patient, a reservoir for collecting received blood, a flow path between the suction wand and the reservoir, and an anticoagulant pump and line for introducing anticoagulant into the flow path upstream of the reservoir. Sensors detect pressure in the flow path and in the anticoagulant line, and transmit corresponding pressure signals to a controller that regulates anticoagulant introduction as a function of the pressure signals.

17 Claims, 5 Drawing Sheets

U.S. PATENT DOCUMENTS

| | | |
|---|---|---|
| 4,658,834 | 4/1987 | Blankenship et al. . |
| 4,769,001 | 9/1988 | Prince . |
| 4,828,543 | 5/1989 | Weiss et al. ............................ 604/4 |
| 4,850,998 | 7/1989 | Schoendorfer . |
| 4,867,738 | 9/1989 | Mintz . |
| 4,923,449 | 5/1990 | Toya et al. . |
| 4,995,268 | 2/1991 | Ash et al. . |
| 5,035,865 | 7/1991 | Inaba et al. . |
| 5,055,198 | 10/1991 | Shettigar . |
| 5,092,836 | 3/1992 | Polaschegg . |
| 5,116,312 | 5/1992 | Blankenship et al. . |
| 5,141,493 | 8/1992 | Jacobsen et al. . |
| 5,227,049 | 7/1993 | Chevsllet et al. ....................... 604/4 |
| 5,378,227 | 1/1995 | O'Riordan et al. ..................... 604/4 |
| 5,403,272 | 4/1995 | Deniega et al. ......................... 604/4 |
| 5,421,812 | 6/1995 | Langley et al. ......................... 604/4 |
| 5,421,815 | 6/1995 | Noguchi et al. ........................ 604/4 |
| 5,423,738 | 6/1995 | Robinson et al. ....................... 604/4 |

BIOLOGICAL/PHARMACEUTICAL METHOD AND APPARATUS FOR COLLECTING AND MIXING FLUIDS

This is a continuation-in-part of U.S. patent application Ser. No. 07/928,040, filed Aug. 11, 1992 now U.S. Pat. No. 5,378,277.

BACKGROUND OF THE INVENTION

1. Field of the Invention

The invention relates generally to an apparatus and method for collecting and mixing two biological/pharmaceutical liquids. The invention may be used in connection with a method and apparatus for collecting whole blood from a donor and mixing the blood with anticoagulant fluids.

2. Description of the Related Art

During surgical procedures, blood is suctioned from surgical cavities using a suction wand that is connected to a blood reservoir for collecting the aspirated blood for later return to the patient. When handling blood in an extracorporeal device, blood readily tends to clot, making it unacceptable for reinfusion into a patient. Thus, it is often desirable to add an anticoagulant to the blood as it is aspirated. Typically, anticoagulant is added proximate the point of initial collection, such as through a side port of the suction wand or into a blood flow passageway adjacent to the suction wand.

In the conventional system, the suction wand is permanently in fluid communication with the blood reservoir where typically, in the case of a hard shell reservoir, a partial vacuum is created. When the suction wand is used, the infusion of anticoagulant is manually controlled by an operator.

If large influxes of blood are encountered during a procedure, it is up to the operator to recognize that additional anticoagulant is needed, and appropriately adjust the anticoagulant flow rate. In general, the operator will try to maintain a fixed ratio of anticoagulant to blood. The target ratio is usually predetermined based upon the anticoagulant being used and any other relevant data (e.g., the type of surgical procedure).

A drawback of this system is its inaccuracy. Because the flow rate and volumes of anticoagulant are manually controlled by the operator using a roller clamp on flexible tubing, the procedure has a high degree of variability. Not only are the initial settings inexact, they have a tendency to change with time caused by changes in the tubing, fluid height changes, and pressure changes in the system.

Another drawback of the related art system is that it does not fit the erratic occurrence and variable flow rate of blood losses, whereas each time the suction wand is used, varying amounts of anticoagulant are usually needed. For example, more anticoagulant is needed as the suction wand draws only blood than when the wand draws a combination of blood and air. However, with the conventional system, unless an operator intervenes, the same amount of anticoagulant is infused into the blood passageway regardless of the amount of blood being suctioned. Even if an operator intervenes, it is difficult to manually achieve a target ratio. Thus, with the conventional apparatus and method, it is possible to infuse too much or too little anticoagulant into the blood, which could lead to dangerous medical conditions.

SUMMARY OF THE INVENTION

Accordingly, the present invention is directed to a blood collection method and apparatus that substantially obviates one or more of the problems due to limitations and disadvantages of the related art.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

To achieve the objectives and in accordance with the purposes of the invention, as embodied and broadly described herein, the apparatus of the invention comprises means for receiving blood from a patient, a reservoir for collecting received blood, means for transporting received blood from the receiving means to the reservoir, means for introducing anticoagulant into the received blood at a predetermined infusion rate, means for detecting at least one pressure value in a blood flow path and at least pressure value in the anticoagulant introducing means, and for generating pressure signals in accordance therewith, and control means for receiving the pressure signals and for varying the predetermined infusion rate of the anticoagulant introducing means as a function of the pressure signals.

In addition, the method of the invention comprises the steps of receiving blood from a patient, collecting the received blood in a reservoir, introducing anticoagulant into a blood flow path, monitoring a flow path pressure value and an anticoagulant pressure value, and regulating introduction of anticoagulant into the flow path as a function of the pressure values in order to control a mixture of ratio of anticoagulant to blood.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention, and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
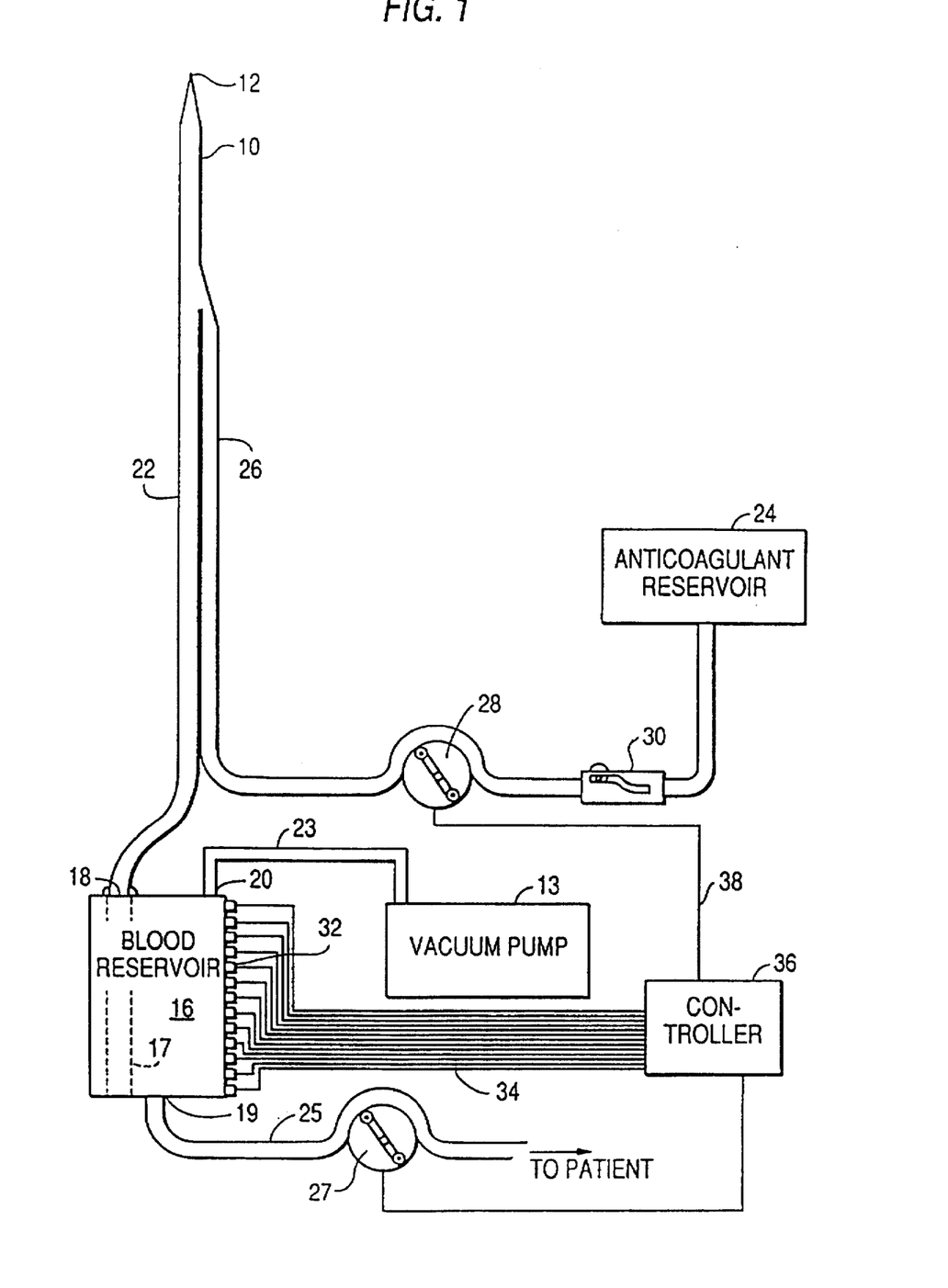
FIG. 1 is a schematic diagram of a blood collection apparatus in accordance with the present invention.

In accordance with the invention there is provided a blood collection apparatus including means for receiving blood from a patient. As embodied herein, and as illustrated in FIG. 1, the blood receiving means includes suction wand 10 such as those conventionally used to suction blood and other fluids from surgical cavities. Suction wand 10 includes an opened end 12 for suctioning blood.

In accordance with the invention there is also provided a reservoir for collecting received blood, and means for transporting received blood to the reservoir. As embodied herein, the transporting means includes tubing segment 22 which connects blood reservoir 16 with suction wand 10, and pump means such as a peristaltic pump or a vacuum pump for conveying fluid through tubing segment 22.

According to a first embodiment of the invention, the pump means includes vacuum pump 13, and blood reservoir 16 includes a hard outer shell constructed, for example, of plastic. As illustrated in FIG. 1, blood reservoir 16 also includes vacuum port 20, inlet port 18, and outlet port 19. Inlet port 18 is connected to tubing segment 22, vacuum port 20 is connected to vacuum pump 13 through tubing segment 23, and outlet port 19 is connected to tubing segment 25 for returning collected blood to the patient or conveying it to a blood treatment device. The opened end 12 of suction wand 10 is permanently in fluid communication with vacuum pump 13, whereby fluid can be suctioned through wand 10 and tubing segment 22 into blood reservoir 16. Similarly, in the embodiment of FIG. 4, the pump means includes peristaltic pump 42, directly located in tubing segment 22 for pumping fluid from suction wand 10 into blood reservoir 16.

Blood reservoir 16 may also include a filter 17 extending from inlet port 18 along the interior length of the reservoir. Not only does filter 17 catch any blood clots that may have formed, but it also dampens fluid flow into the reservoir to prevent waves and splashes. Preferably, a peristaltic pump 27 is provided in tubing segment 25 for emptying the blood reservoir 16, and returning the blood directly to the patient, or conveying it to a device for further processing.

While the preferred embodiments of the present invention are described in connection with the suctioning of blood from surgical cavities, the invention has broad medical applications. Even when used in the medical field, the invention is not limited to a suctioning apparatus, but may be used in other types of extracorporeal blood circuits and blood collection devices. For example, in certain applications, in lieu of the suction wand, the blood receiving means may include a blood collecting needle for receiving blood from the arterio-venous system of a patient.

Also in accordance with the invention there is provided means for introducing anticoagulant into the blood at a predetermined infusion rate. As embodied herein, the anticoagulant introducing means includes anticoagulant reservoir 24 connected to suction wand 10 via tubing segment 26. Anticoagulant reservoir 24 is typically used for holding a volume of anticoagulant such as heparin or citrate. A pump, such as a variable speed peristaltic pump 28, engages tubing segment 26 for pumping anticoagulant through tubing segment 26 and into tubing segment 22. In addition, a roller clamp 30 may be provided in tubing segment 26 to permit manual restriction of anticoagulant flow in the event of system failure. As is discussed later in greater detail, the speed of pump 28 is controlled to achieve a predetermined infusion rate for the anticoagulant.

Tubing segments 22 and 26 may be joined in a "Y" configuration adjacent suction wand 10. This structure permits anticoagulant to be added to the blood immediately as it is suctioned from a surgical cavity so that coagulation may be prevented as blood travels through tubing segment 22.

Figure 2:
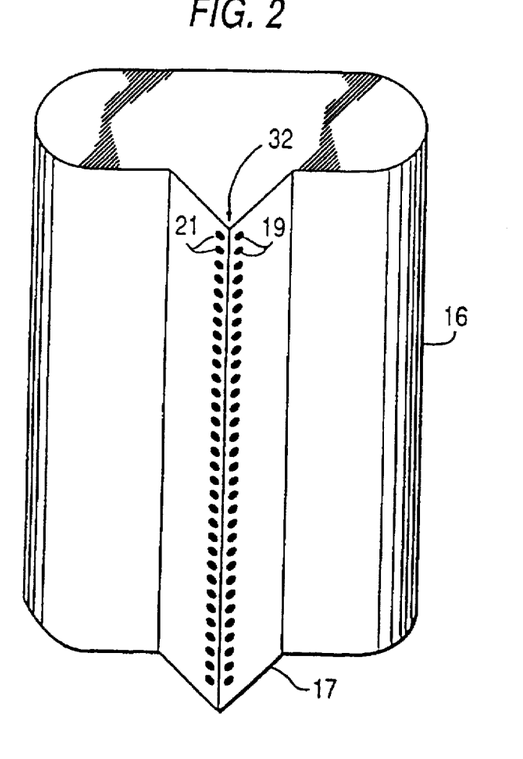
FIG. 2 is a perspective view of the blood reservoir depicted in FIG. 1.
Figure 3:
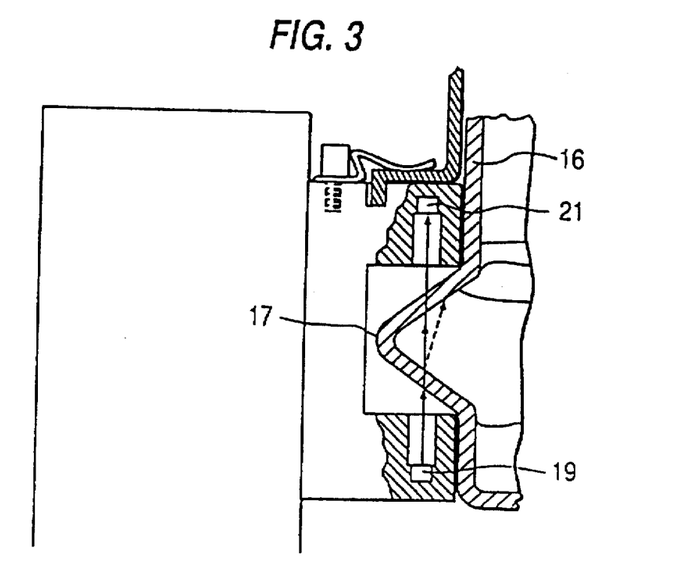
FIG. 3 is a fragmentary sectional view showing a detail of the blood reservoir depicted in FIG. 2.

In accordance with the present invention there is also provided means for sensing liquid volume in the reservoir and for transmitting a volume signal corresponding thereto. As embodied herein, and as best illustrated in FIGS. 2 and 3, the sensing means includes an array of optical detectors 32 extending vertically along blood reservoir 16. For example, optical detectors 32 may include a set of thirty-two pairs of light emitting diodes 19 and phototransistors 21. The detector pairs are arranged to sense the presence of fluid at their individual height. According to a preferred embodiment, the detector pairs are spaced from each other at 100 ml intervals. The bottom sensor is placed at a volume of 100 ml. Therefore, the volume in the reservoir can be detected within ±50 ml.

Reservoir 16, illustrated in FIG. 2, is substantially elliptical in cross-section and includes a V-shaped protrusion 17 extending in the vertical direction of the reservoir. Preferably, the walls of the V-shaped protrusion are oriented at a 90° angle to each other. The array of optical detectors 32 are arranged along V-shaped protrusion 17 so that each of the light emitting diodes 19 is oriented opposite a corresponding phototransistor 21. Liquid volume sensed by optical detectors 32 is converted into an electrical signal which is transmitted through one of signal lines 34.

In accordance with the invention there is provided control means for regulating the anticoagulant introducing means in accordance with a predetermined program and as a function of the volume signal. As embodied herein and as illustrated in FIG. 1, the control means includes controller 36 electrically connected to each of the array of optical detectors 32 through signal lines 34 for receiving the volume signal from the array. Controller 36 is also connected through signal line 38 to peristaltic pump 28, and includes a microprocessor that is programmed with an algorithm to automatically administer anticoagulant by regulating pump 28 in response to the level detected in blood reservoir 16. Preferably, the program of the microprocessor includes an algorithm which filters out "noise" which may occur when the reservoir is inadvertently bumped and waves move through the blood supply.

In a preferred embodiment, the blood reservoir has a capacity of approximately 3.2 liters with detectors spaced along the vertical direction of the reservoir at 100 ml intervals. The average salvage rate may be calculated at each occurrence of detection by any sensor, as follows:

$$Qb=(Vinc+Vpump-Vac)/Time$$

where Qb=average rate of blood salvage at the most recent sensor change,

Vinc=change in volume in reservoir during sensor change, acceptable values are +100, −100, or 0 ml, Vpump=volume pumped out of reservoir since previous sensor change, Vac=volume of anticoagulant pumped into reservoir since previous sensor change, and Time=time elapsed from previous sensor change.

As previously indicated, Vinc is a function of the level detected by the array of sensors 32, and corresponds to the change in fluid height in the reservoir. Vpump and Vac are calculated as a function of the number of respective pump revolutions (pumps 27 and 28).

Between sensor changes it is possible to calculate the maximum (Qb max) and minimum (Qb min) average salvage rates that could occur. These values are given by:

$$Qb\ max=(V+Vpump-Vac)/Time$$

$$Qb\ min=(V-100\ ml+Vpump-Vac)/Time$$

where Vpump, Vac, and Time have similar definitions as above except that they are for the time interval since the most recent change, and where V=100 ml if the most recent sensor change indicated that the reservoir level was increasing, and V=0 ml if the most recent sensor change indicated that the reservoir level was decreasing. Between sensor changes the current estimate of Qb is assumed to equal the last calculated value for Qb unless it exceeds one of the bounds as defined by Qb max or Qb min in which case Qb is set equal to that bound.

With the above-described system, anticoagulant can be automatically delivered as a function of either volume of blood salvaged or the salvage rate. Given that the current desired practice is to anticoagulate salvaged blood at a specific ratio, one part anticoagulant to R parts of salvaged blood, the pump in a preferred embodiment may be set to run at Qb divided by the ratio but not less than a predetermined drip rate. The ratio is also selected by the operator and can be changed as desired.

Figure 4:
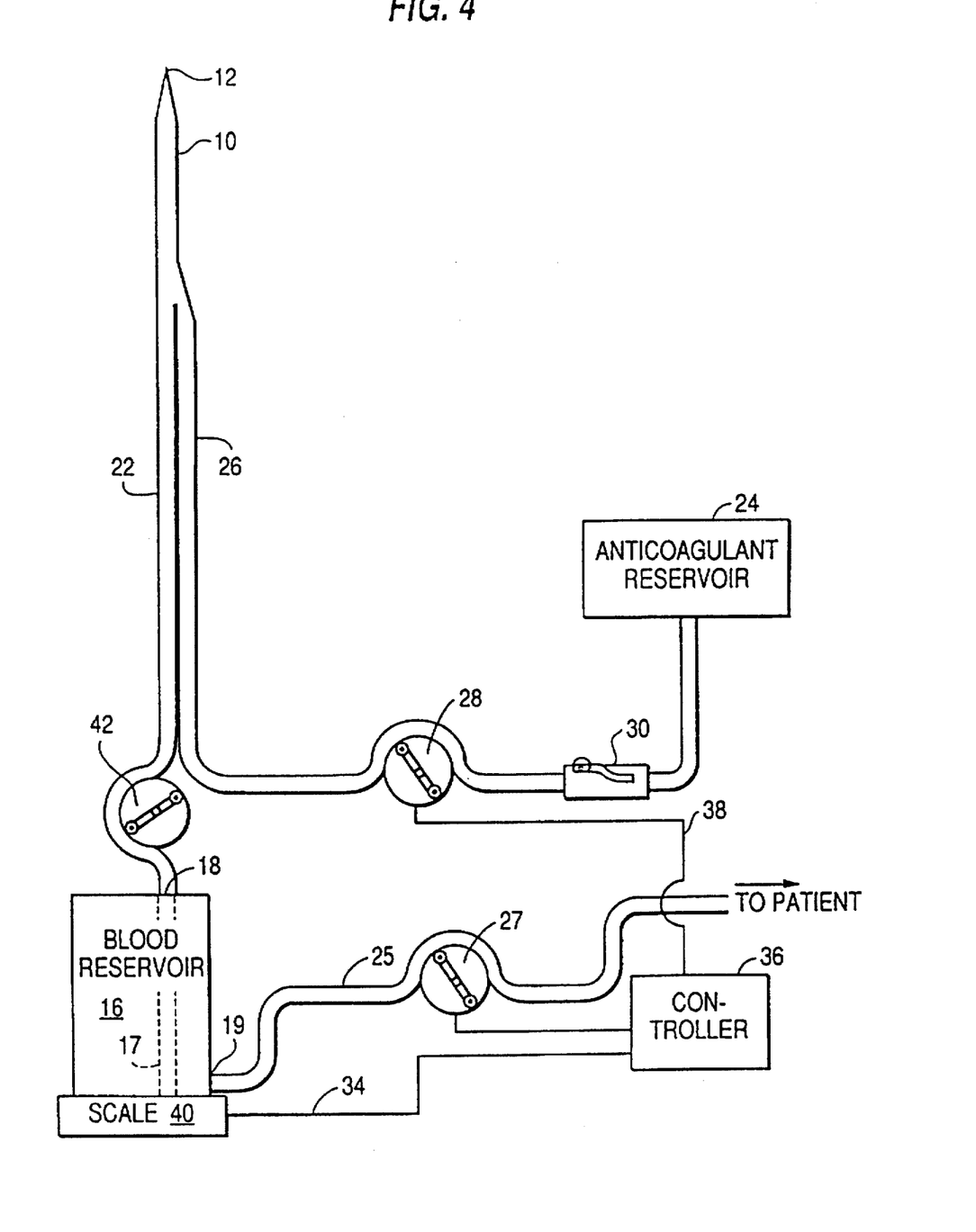
FIG. 4 is a schematic diagram of a second embodiment of the present invention.

An alternative preferred embodiment, depicted in FIG. 4, employs a scale 40 in lieu of an array of detectors for detecting blood volume in reservoir 16. An algorithm can be constructed by one skilled in-the art to calculate the salvage rate and/or volume in the blood reservoir based upon known weights of anticoagulant and blood and the known volume of infused anticoagulant. In the embodiment of FIG. 4, since an array of detectors is not needed, blood reservoir 16 may include a conventional flexible plastic blood bag. If a blood bag is used, a peristaltic pump 42 is located in tubing segment 22 as illustrated in FIG. 3, as a substitute for vacuum pump 13 (illustrated in FIG. 1) which would otherwise collapse a plastic blood bag in absence of an additional support. Pump 42 could also be used in connection with the embodiment of FIG. 1 in lieu of vacuum pump 13, if desired.

In the embodiments described above there is a slight delay in anticoagulant introduction because anticoagulant flow rate is adjusted after the blood reaches the reservoir. While such systems are far more precise than those available prior to this invention, the following embodiments depicted in FIGS. 5 and 6 may provide even greater precision.

Figure 5:
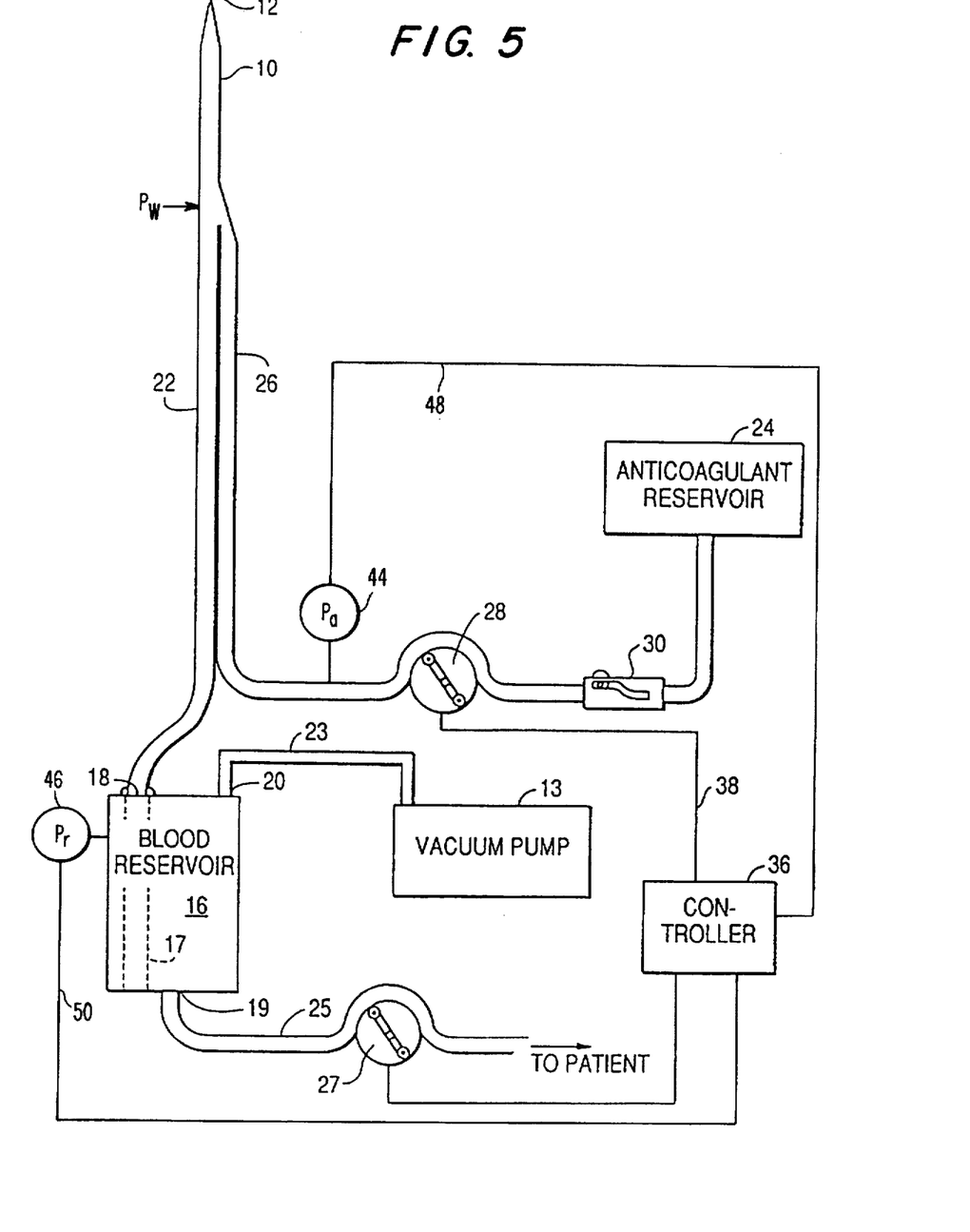
FIG. 5 is a schematic diagram of a third embodiment of the present invention.

The embodiment of FIG. 5 includes many of the same features as the first two embodiments. One point of departure is that in lieu of the array of detectors, the embodiment of FIG. 5 includes means for detecting at least one pressure value in the extracorporeal flow path and at least one pressure value in the anticoagulant introducing means, and for generating pressure signals in accordance therewith. As illustrated in FIG. 5, the pressure detecting means may include a pressure gauge 46 that senses a pressure $P_r$ in the blood reservoir 16 and a pressure gauge 44 that senses a pressure $P_a$ in tubing segment 26 between pump 28 and suction wand 10. Pressure gauge 46 can also be placed at other points along tubing segment 22 except for the intersection of tubing segment 22 with tubing segment 26. If placed in tubing segment 22, pressure gauge 46 is preferably positioned at a point sufficiently spaced from suction wand 10 to measure the pressure drop along tubing segment 22. The pressure $P_w$ at the wand is not a measured parameter but is calculated and used as described later. Of course rather than calculating $P_w$, the invention could be constructed with an additional pressure gauge (not shown) to obtain actual pressure readings at the wand.

The pressure drop down tubing segment 22 between the point at which anticoagulant enters tubing segment 22 and the inlet port 18 of reservoir 16 is a function of the flow rate of blood, air, or a mixture of blood and air through tubing segment 22, and can be expressed as follows:

$$P_w - P_r = f(\text{blood flow through tubing segment 22})$$

where f() is a function which can be determined empirically by, for example, an algorithm. As is described later in greater detail, the pressure difference can be used to determine a desired anticoagulant introduction rate.

The anticoagulant solutions conventionally used are Newtonian fluids and the flow rates are typically in the laminar region. Therefore, the pressure drop down the anticoagulant line can be expressed in terms of the following equation.

$$P_a - P_w = cQ_a$$

where c is a constant dependent upon the viscosity of the anticoagulant solution and the inside diameter of tubing segment 26 and where $Q_a$ is the anticoagulant flow rate. Combining the above two equations shows that by knowing the anticoagulant flow rate, the pressure difference between tubing segment 26 and reservoir 16 is a function of the blood flow through tubing segment 22, i.e., the blood salvage rate.

$$P_a - P_r = cQ_a + f(\text{blood flow through tubing segment 22})$$

In operation, gauges 44 and 46 transmit to controller 36 via lines 48 and 50, respectively, signals corresponding to the detected pressures. In addition, the speed of pump 28 (i.e., the anticoagulant flow rate) is monitored by controller 36 via line 38. Since $P_a$, $P_r$, and $cQ_a$ can be measured, the blood salvage rate can be calculated using the equation above. Once blood flow through the suction wand is detected by the two pressure gauges, controller 36 can regulate pump 28 to provide the desired anticoagulant flow rate according to a predetermined algorithm.

In accordance with the invention there is provided control means for receiving the pressure signals and for varying the predetermined infusion rate of the anticoagulant introducing means as a function of the pressure signals to thereby regulate a mixture ratio of anticoagulant to blood. There are many possible ways that detected or calculated pressures in the flow path can be used to extrapolate the blood flow rate and thereby be indicative of a desired anticoagulant infusion rate. One example which employs two pressure measurements ($P_a$ and $P_r$) is illustrated below. It must be understood that the invention in its broadest sense is not limited to the following algorithm. Other algorithms using one or more pressure readings are also contemplated.

Figure 6:
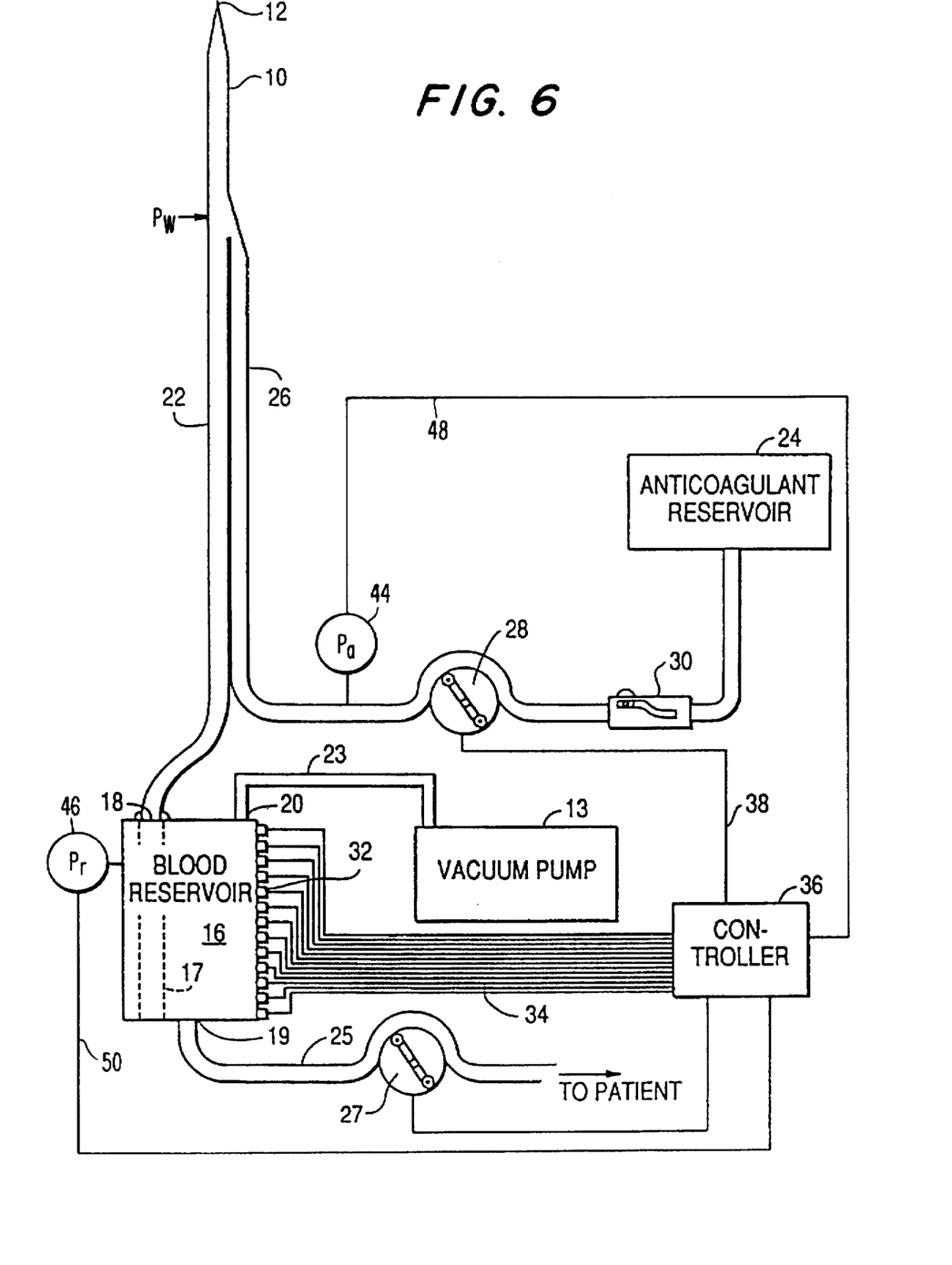
FIG. 6 is a schematic diagram of a fourth embodiment of the present invention.

The following exemplary algorithm is described in connection with the embodiment of FIG. 6, which includes both the optical detectors of FIG. 1 and the pressure gauges of FIG. 5. The following algorithm, however, could easily be modified to use only pressure readings.

A. The pressures $P_a$ and $P_r$ (measured in mmHg) plus the anticoagulant pump flow rate $Q_a$ (measured in mL/min) are read by software every 60 msec. The algorithm starts after priming the reservoir (or after calibration of volume sensors if not priming).

B. The pressure at the wand $P_w$ is defined as follows:

$P_w = P_a - CQ_a$ where c=a constant dependent on the tubing used (e.g., 0.30).

C. Baseline: Baseline values for $P_w$ and $P_r$ are calculated as follows:

$P_{wb}$=Average of last 500 values of $P_w$ for which Flags 1, 2, and 3 (defined below) equal zero and $Q_a \leq 10$.

$P_{rb}$=Average of last 500 values of $P_r$ for which Flags 1, 2, and 3 equal zero and $Q_a \leq 10$.

D. If vacuum pump 13 is being used (assume it is being used if it is turned on) then the wand and reservoir pressures must be averaged as follows. If the vacuum pump 13 is cycling (i.e., port 20 is opened) then the average must be taken using the number of readings (n) corresponding to one period. If the pump is not cycling (or the vacuum is not on) then use the present value, i.e., n=1. The maximum value allowed for n is 60, for longer periods set n=1.

$$P_{wa} = \sum_{i=1}^{i=n} P_w/n \quad \text{and} \quad P_{ra} = \sum_{i=1}^{i=n} P_r/n$$

E. Pressures relative to the baseline are defined as follows:
$P_{wo}=P_{wa}-P_{wb}$
$P_{ro}=P_{ra}-P_{rb}$
$\Delta P_o=P_{wo}-P_{ro}$ F. Flags: Flags 1, 2, and 3 are defined equal to zero for the first 500 values stored in baseline. Thereafter, they are defined as follows:

Wand Blocked: Flag 1=1 if $P_{ro}<-20$ and $P_{wo}<-20$ and $\Delta P_o<0$.

Flag 1=2 if the above conditions remain true for greater than 50 consecutive data readings. Otherwise, Flag 1=0.

Reservoir Blocked: Flag 2=1 if $P_{ro}<-20$ and $P_{wo}>0$ and $\Delta P_o>20$ otherwise Flag 2=0.

Flow Condition: Flag 3=1 if $P_{ro}<-20$ and $P_{wo}<-10$ and Flag 1 <>2 and the number of volume changes since the beginning of this particular event is less than 2. Otherwise, Flag 3=0. "This particular event" is not over until either $P_{ro}>-20$ or $P_{wo}>-10$.

G. If Flag 3=1 then set $Q_{a.(pump)}=30$ mL/min otherwise set $Q_{a.(pump)}=0$. This value should be compared to the $Q_a$ from the volume level detector illustrated in FIG. 1. The higher value should be used to control the anticoagulant pump. Note, if the anticoagulant pump is currently running at 30 mL/min or greater this algorithm still needs to be executed so that $P_{wa}$ and $P_{ra}$ will be calculated.

H. If Flag 3=1 continuously for a time greater than volume divided by 100 mL/min then the algorithm should be restarted so that a new baseline will be calculated. The volume to be used is the current volume between sensors.

I. If a volume change occurs for which $Q_a$ is set to 50 mL/min or greater and Flag 3 was not equal to 1 at least once since the previous volume change then restart the algorithm so that a new baseline will be calculated.

J. If there has not been a volume change in 5 minutes and Flag 1>0 for the entire 5 minutes then restart the algorithm.

K. If there has not been a volume change in 5 minutes and Flag 2=1 for the entire 5 minutes then restart the algorithm.

L. If the operator resets the vacuum level restart the algorithm.

In each of the embodiments, the control means may also include input means, such as a keypad (not shown), for permitting an operator to select various parameters of anticoagulant infusion. For example, the input means may permit a user to set minimum pump speed, a target ratio, or may even permit manual control by completely overriding the programmed algorithm.

In another embodiment (not illustrated), the receiving and transporting means may be a sponge that is used to absorb blood from the surgical cavity and is then manually squeezed into a basin from whence it is transferred into the blood reservoir. When the sensing means detects the increased volume in the reservoir, the control means directs an appropriate amount of anticoagulant directly into the blood reservoir.

While the invention is described in connection with the infusion of anticoagulant into blood, the invention is not intended to be limited to such uses. For example, the invention has broad applications to other medical systems which will be apparent to those skilled in the art and which may be constructed without departing from the scope and spirit of the invention. Additionally, rather than using an array of optical detectors 32, scale 40, or pressure gauges 44 and 46 to monitor accumulation of blood and anticoagulant in reservoir 16, a flow detector may be placed in tubing segment 22 to monitor the rate of flow into the reservoir. The monitored rate of flow and an appropriate clock for detecting the length of time the flow rates occur can be used to determine very accurately the amount of blood being suctioned, and the flow of anticoagulant can be infused in accordance therewith. Thus, it is intended that the specification and examples be considered as exemplary only, with a true scope and spirit of the invention being indicated by the following claims.

What is claimed is:

1. A blood collection apparatus including an extracorporeal flow path, the apparatus comprising:
   means located in the flow path for receiving blood from a patient;
   a reservoir located in the flow path downstream of the receiving means, the reservoir for collecting received blood;
   means for transporting received blood from the receiving means to the reservoir;
   means connected to the flow path for introducing anticoagulant into the received blood at a predetermined infusion rate before the blood leaves the reservoir;
   means for detecting a first pressure value in the extracorporeal flow path and for generating a first pressure signal in accordance therewith, and for detecting a second pressure value in the anticoagulant introducing means, and for generating a second pressure signal in accordance therewith; and
   control means for receiving the first and second pressure signals and for varying the predetermined infusion rate of the anticoagulant introducing means as a function of the first and second pressure signals.

2. An apparatus according to claim 1, wherein the detecting means includes a first pressure sensor for generating the first pressure signal relating to a pressure value in the reservoir, and a second pressure sensor for generating the second pressure signal relating to a pressure value in the anticoagulant introducing means, and wherein the control means varies the predetermined infusion rate as a function of a difference between the first pressure signal and the second pressure signal.

3. An apparatus according to claim 1, wherein the receiving means includes a suction wand, and the transporting means includes pump means for drawing blood through the suction wand and a conduit flow connecting the suction wand and the reservoir.

4. An apparatus according to claim 3, wherein the pump means is a vacuum pump for establishing a negative pressure within the reservoir to induce flow into the reservoir.

5. An apparatus according to claim 3, wherein the pump means includes a peristaltic pump located between the receiving means and the reservoir.

6. An apparatus according to claim 1, wherein the anticoagulant introducing means includes an anticoagulant reservoir in fluid communication with the blood collecting reservoir.

7. An apparatus according to claim 6, wherein the anticoagulant introducing means further includes a variable speed pump, and wherein the control means regulates the speed of the pump as a function of the first and second pressure signals.

8. An apparatus according to claim 1, wherein the control means includes a predetermined program, and further including input means connected to the control means for permitting a user to vary the predetermined program.

9. An apparatus according to claim 1, further including means for sensing liquid volume in the reservoir and for transmitting a volume signal corresponding thereto, and wherein the control means further includes means for calculating a rate of volume change of fluid in the reservoir and means for regulating the flow of anticoagulant as a function of the calculated rate of volume change and the pressure signal.

10. A method for collecting blood from a patient employing an extracorporeal flow path, the method comprising the steps of:

receiving blood from a patient;

transporting the received blood to a reservoir in the flow path;

introducing anticoagulant into the flow path via a conduit;

monitoring a first pressure value at at least one location in the flow path;

monitoring a second pressure value in the conduit; and regulating introduction of anticoagulant into the flow path as a function of the first and second pressure values in order to control a mixture ratio of anticoagulant to blood.

11. A method according to claim 10, wherein the step of receiving includes the substep of suctioning blood through a suction wand.

12. A method according to claim 10, wherein the step of introducing includes the substep of introducing the anticoagulant with a pump, and wherein the step of regulating includes the substep of controlling a speed of the pump.

13. A method according to claim 10, wherein the step of regulating includes controlling anticoagulant introduction in accordance with a predetermined program that is variable in response to data supplied by a user.

14. An apparatus, including an extracorporeal flow path, for controlling flow of a medical fluid into flow of a biological fluid, the apparatus comprising:

a fluid reservoir in the flow path;

transporting means for conveying the biological fluid into the fluid reservoir;

conduit means flow connected to the transporting means, for conveying the medical fluid into the transported biological fluid;

means for detecting a first pressure value in the flow path and for detecting a second pressure value in the conduit means; and control means for varying the medical fluid flow as a function of the detected first and second pressure values to thereby regulate a mixture ratio of biological fluid to medical fluid.

15. A method, employing a main flow path, for controlling flow of a medical fluid into a flow of a biological fluid, the method comprising the steps of:

transporting along the flow path the biological fluid to a reservoir located in the flow path;

introducing medical fluid into the flow path via a conduit;

monitoring a first pressure value in the flow path;

monitoring a second pressure value in the conduit; and regulating introduction of the medical fluid into the flow path as a function of the first and second pressure values in order to regulate a mixture ratio of the medical fluid to the biological fluid.

16. A method according to claim 15, wherein the medical fluid includes anticoagulant and the biological fluid includes blood.

17. An apparatus according to claim 14, wherein the medical fluid includes anticoagulant and the biological fluid includes blood.

* * * * *